(12) United States Patent
Piergiorgio et al.

(10) Patent No.: US 10,874,779 B2
(45) Date of Patent: Dec. 29, 2020

(54) ARTIFICIAL HEART AND ITS DRIVE UNIT

(71) Applicant: CENTRE HOSPITALIER UNIVERSITAIRE VAUDOIS

(72) Inventors: Tozzi Piergiorgio, Lausanne (CH); Jonathan Emery, Lens (CH); Audrey Maertens, Lausanne (CH); Francois Avellan, Lausanne (CH); Vincent Berruex, Lausanne (CH)

(73) Assignee: Centre Hospitalier Universitaire Vaudois (C.H.U.V.), Lausanne (CH)

( * ) Notice: Subject to any disclaimer, the term of this patent is extended or adjusted under 35 U.S.C. 154(b) by 120 days.

(21) Appl. No.: 16/093,410

(22) PCT Filed: Apr. 5, 2017

(86) PCT No.: PCT/EP2017/058154
§ 371 (c)(1),
(2) Date: Oct. 12, 2018

(87) PCT Pub. No.: WO2017/178307
PCT Pub. Date: Oct. 19, 2017

(65) Prior Publication Data
US 2019/0167872 A1 Jun. 6, 2019

(30) Foreign Application Priority Data

Apr. 12, 2016 (EP) .................................... 16164929

(51) Int. Cl.
*A61M 1/10* (2006.01)
(52) U.S. Cl.
CPC ............ *A61M 1/1005* (2014.02); *A61M 1/10* (2013.01); *A61M 1/1012* (2014.02); *A61M 1/1036* (2014.02); *A61M 2205/04* (2013.01)
(58) Field of Classification Search
CPC ....................................................... A61M 1/10
See application file for complete search history.

(56) References Cited

U.S. PATENT DOCUMENTS 6,527,698 B1    3/2003 Kung et al.

FOREIGN PATENT DOCUMENTS

DE          4325166 A1    2/1995
WO    2005105177 A2    11/2005
(Continued)

*Primary Examiner* — Matthew W Schall
(74) *Attorney, Agent, or Firm* — Dinsmore & Shohl LLP; Weston R. Gould

(57) ABSTRACT

There is described an artificial heart comprising a pump, the pump comprising a housing (10) defining a substantially spherical cavity and comprising four vascular connectors ($15_{in}$, $15_{out}$, $15'_{in}$, $15'_{out}$), namely two inlet connectors ($15_{in}$, $15'_{in}$) and two outlet connectors ($15_{out}$, $15'_{out}$) to connect the pump to the pulmonary and systemic circulation. A rotatable disc (11) is mounted within the housing (10) and secured to rotate about a fixed axis (12). Two oscillating palettes (16a, 16b) are mounted to rotate about a mobile axis (17) movable within a plane perpendicular to the fixed axis (12), wherein said palettes (16a, 16b) are connected together and are arranged on both sides of the rotatable disc (11), in a diametrically opposed fashion, to create two pumping units comprising each two variable sized chambers (20a, 20b, 20c, 20d) in fluid communication with one corresponding inlet and outlet connector respectively. The pump is provided with constrain means (21) configured to cause an oscillating movement of each oscillating palette (16a, 16b) relative to the rotatable disc (11), when the pump is operating, in order to produce simultaneously two suction strokes and two discharge strokes, so as to pump blood from the inlet connectors ($15_{in}$, $15'_{in}$) into one chamber (20a, 20c) of each pumping unit while expelling blood from the other chamber (20b, 20d) of each pumping unit through the outlet connectors ($15_{out}$, $15'_{out}$). The pump further comprises a drive unit configured to operate the pump. According to the invention the drive unit is configured to produce a rotating magnetic field inside the pump housing (10).

10 Claims, 5 Drawing Sheets

(56) References Cited

FOREIGN PATENT DOCUMENTS

| WO | 2009053764 A1 | 4/2009 |
| WO | 2012002816 A2 | 1/2012 |

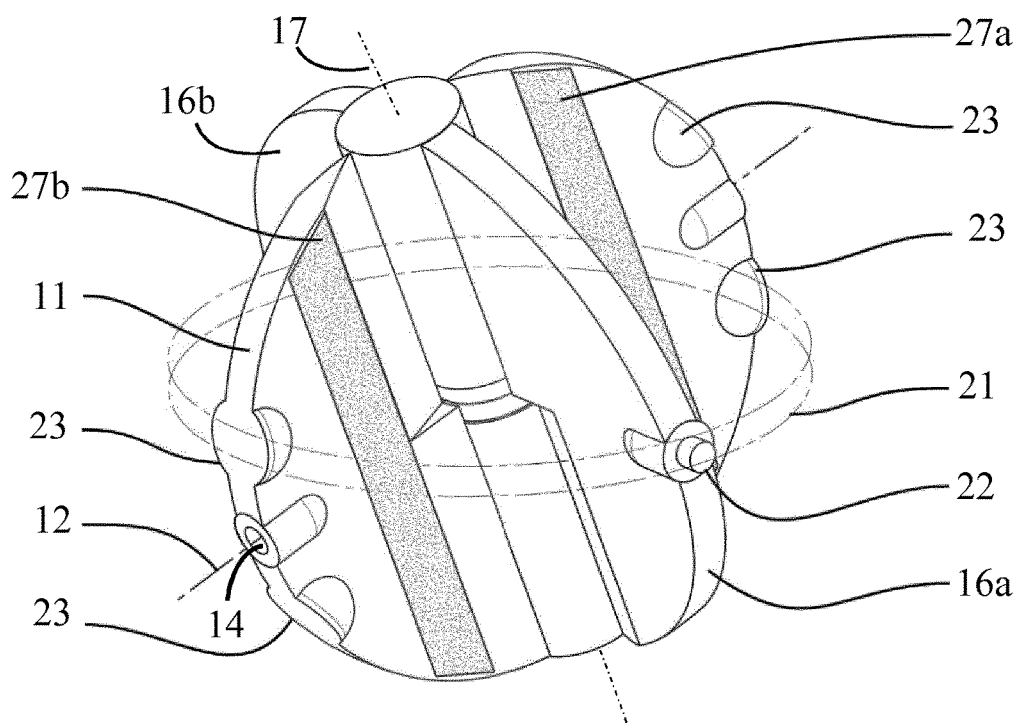
*Fig. 5a*
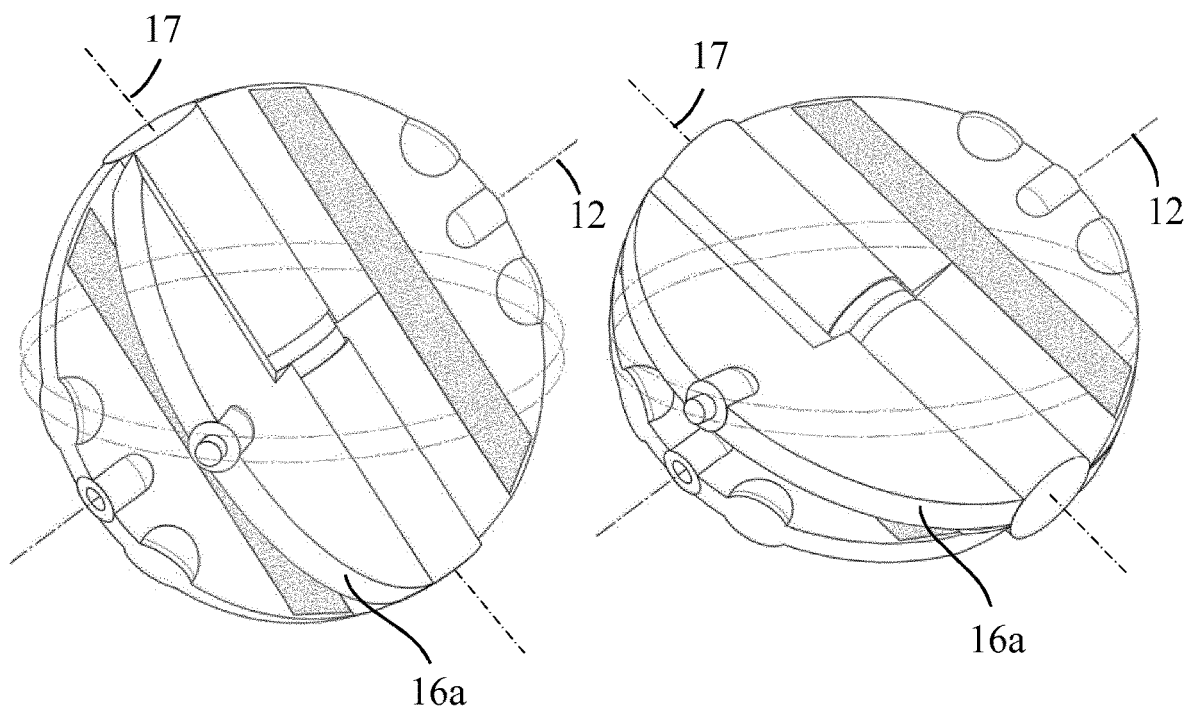
*Fig. 5b*  *Fig. 5c*

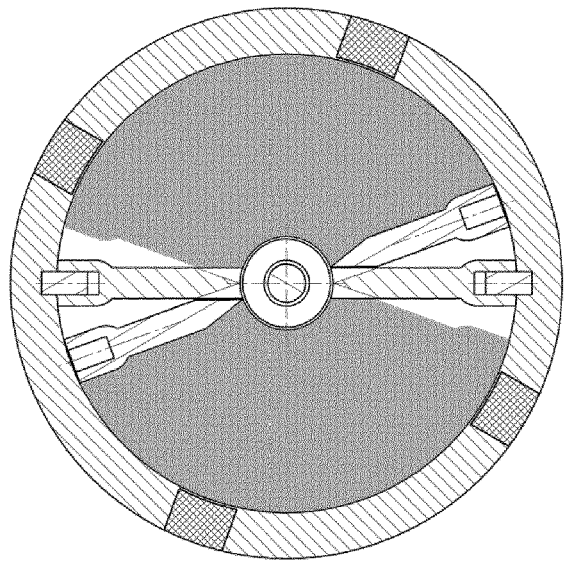 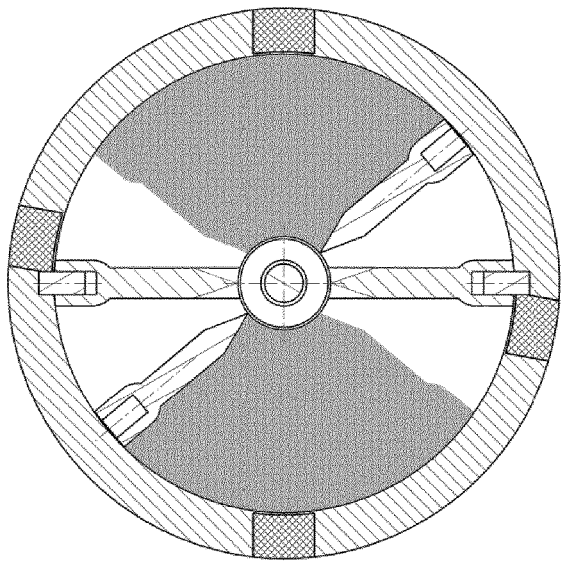
*Fig. 8a*          *Fig. 8b*
*Fig. 9*
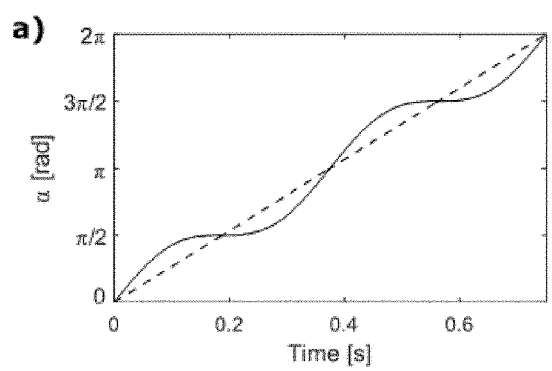 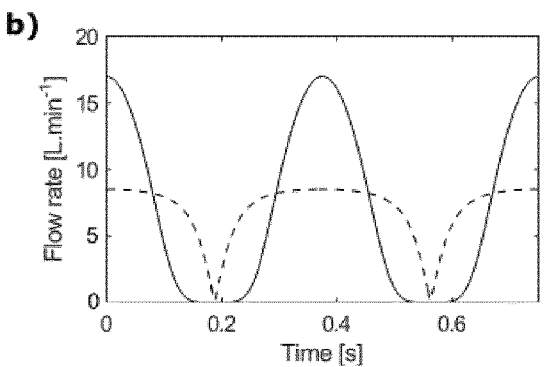

ARTIFICIAL HEART AND ITS DRIVE UNIT

FIELD OF THE INVENTION

The invention generally relates to cardiovascular implants, and more particularly to an artificial heart and its drive unit that completely replace a failing heart to provide blood flow to the pulmonary and systemic circulation.

BACKGROUND OF THE INVENTION

Congestive heart failure is a major and growing health problem. Despite the improvement of conventional medical therapy, there remains a large group of patients who have poor prognosis and require more aggressive techniques to increase their quality of life and life expectancy. Heart transplantation and mechanical support of the circulation are two options that can be offered to the most disabled patients who are refractory to a classical treatment or for whom the cardiac function is so severely decreased that they are in cardiogenic shock or depend on inotropic medication. This last approach is rapidly evolving due to the inadequate number of useable donor hearts available.

The mechanical support of the circulation has several indications depending on whether the heart must be assisted for a short, intermediate or long-term period. There exists a lot of devices to help or substitute the function of the heart which are divided in different categories, each with particular objectives, advantages and disadvantages. The most widely implanted devices are ventricular assist-devices (VAD), which can be used as a bridge to transplantation to sustain life until a donor heart becomes available, as a bridge to decision regarding transplant eligibility, as destination or permanent therapy, or as a bridge to recovery of heart function.

Nowadays, almost all ventricular assist devices are second generation devices which are axial or centrifugal continuous flow pumps, while first generation devices used pulsatile mechanisms. They are much more durable, smaller, and quieter and hence surgical implantation is generally less traumatic. Continuous flow pumps also have smaller drivelines and hence tend to have lower rates of driveline infection. However, the lack of pulsatility has been correlated to a decrease of right heart recovery, as well as an increase of valve and capillary dysfunction. The remaining problems are caused by the formation of thrombus and haemolysis which is caused by the rotation of mechanical component of the pump. Moreover, these second generation pumps are more sensitive to variation of systemic or pulmonary resistance as their flow capacity depends on the head pressure imposed by the vascular circuit connected to them.

WO2006/067588 discloses an artificial heart which offers significant advantages in terms of reduced size, simplicity and cost over existing devices intended for complete replacement of the heart. This artificial heart is based on a pump comprising a casing defining a spherical cavity which houses a disc, rotatable about a fixed axis, and two oscillating palettes mounted to rotate about a diameter of the rotating disk perpendicular to the fixed axis. These palettes are connected together and arranged on both sides of the disc, in a diametrically opposed fashion, to create two pumping units comprising each two variable sized chambers. This pump further comprises constrain means configured to cause an oscillating movement of each oscillating palette relative to the disc, when the pump is operating, so as to produce simultaneously two suction strokes and two discharge strokes in order to provide blood flow to the pulmonary and system circulation concurrently.

The drive system of the above pump comprises a motor external to the casing. The drive pinion of this motor is geared either with a gear-wheel connected to a shaft supporting the rotatable disc so as to impart an angular movement to the disc about the fixed axis or with a ring gear mounted to rotate relative to the casing within a so-called equator plane, which divides the casing in two hemispheres, and wherein each oscillating palette is hinged on the inner surface of the gear ring in a diametrically opposed manner. Accordingly, the configuration of the pump's drive unit brings the disadvantages of increasing significantly the total size of the artificial heart as well as requiring a motor whose external components are entirely made of biocompatible materials.

Moreover, the angle between the fixed axis of this pump and the equator plane ranges most preferably from 30° to 50°, which has the disadvantage to pump efficiently only a reduced portion of the total pump volume. The number of rotations per minute of the disc about the fixed axis must therefore be increased to respect the volume constraint thereby compromising pulsatility of the flow and increasing the risk of haemolysis.

In addition, the above pump does not take into account the asymmetry between right and left circulation which makes this pump unsuitable for human implant.

SUMMARY OF THE INVENTION

An aim of the present invention is therefore to provide an artificial heart comprising another type of drive unit which overcomes the above disadvantages.

This aim is achieved by an artificial heart including a pump of the type of pump discussed above which thus comprises a housing defining a substantially spherical cavity and comprising four vascular connectors, namely two inlet connectors and two outlet connectors to connect the pump to the pulmonary and systemic circulation. A rotatable disc is housed within the pump housing and secured to rotate about a fixed axis passing through the center of the spherical cavity. Two oscillating palettes are mounted to rotate about a diameter of the rotating disk, perpendicular to the fixed axis. These two palettes are connected together and are arranged on both sides of the rotatable disc, in a diametrically opposed fashion, to create two pumping units comprising each two variable sized chambers in fluid communication with one inlet and one outlet connector respectively. The pump is provided with constrain means configured to cause an oscillating movement of each oscillating palette relative to the rotatable disc, when the pump is operating, in order to produce two concurrent suction strokes simultaneously with two concurrent discharge strokes, so as to pump blood from the inlet connectors into one chamber of each pumping unit while expelling blood from the other chamber of each pumping unit through the outlet connectors. The pump further comprises a drive unit to operate the pump. According to the invention, the drive unit is advantageously configured to produce a rotating magnetic field inside the pump housing which significantly decreases the overall size of the artificial heart.

Another aim of the present invention is to provide an artificial heart comprising a pump with an improved ratio between the pumping capacity and the volume of the pump.

This aim is achieved by an artificial heart including the pump of the type of the pump discussed above irrespective of its driving unit and wherein the fixed axis is inclined at an angle α with respect to the equator plane, wherein the angle α is typically between 10° and 30° degrees, preferably between 10° and 20°, and most preferably between 10° and 15°. The pump can therefore be operated at lower speed than the known pump with an identical volume thereby improving pulsatility of the pump flow and decreasing the risk of haemolysis.

Another aim of the present invention is to provide an artificial heart comprising a pump which takes into account the asymmetry between right and left circulation of the human heart.

This aim is achieved by an artificial heart including the pump of the type of the pump discussed above irrespective of its driving unit and wherein a shunt is arranged to ensure fluid communication between two chambers for balancing the pulmonary and systemic circulation. Optionally, the shunt comprises a valve for adjusting the flux though the shunt.

According to an embodiment of the invention, the drive unit comprises:

two multi-pole stators mounted around the circumference of the housing or embedded, at least partially, in the housing wall to generate a rotating magnetic field inside the pump housing, and at least one permanent magnet arranged on the rotatable disc on both sides of its rotation axis in correspondence with the two multi-pole stators so as to impart a rotating movement to the rotatable disc about the fixed axis through the rotating magnetic field.

According to another embodiment of the invention, the drive unit comprises:

a rotatable ring having several permanent magnets and which is rotatably mounted inside a circular seat arranged in the equator plane of the pump housing, wherein both oscillating palettes are hinged on the inner surface of the rotatable ring in a diametrically opposed fashion, and a multi-pole stator mounted around the housing or embedded, at least partially, in the housing wall concentrically with respect to the rotatable ring so as to impart a rotating movement to the rotatable ring along its circular seat through the rotating magnetic field.

BRIEF DESCRIPTION OF FIGURES

The invention will be better understood thanks to the following detailed description of several embodiments of the invention with reference to the attached drawings, in which:

FIGS. 5a, 5b and 5c show different perspective views of the artificial heart without the pump housing at three intervals of rotation of the rotatable disc;

FIGS. 8a and 8b show a cross sectional view of the artificial heart illustrating dead volume according to a first and a second configuration respectively.

FIGS. 9a and 9b show plots representing the angular position of the motor for a constant and an oscillating rotational velocity and the instant heart-exiting flow rate with a constant and an oscillating rotational velocity motor, respectively.

DETAILED DESCRIPTION OF THE INVENTION

Figure 1:
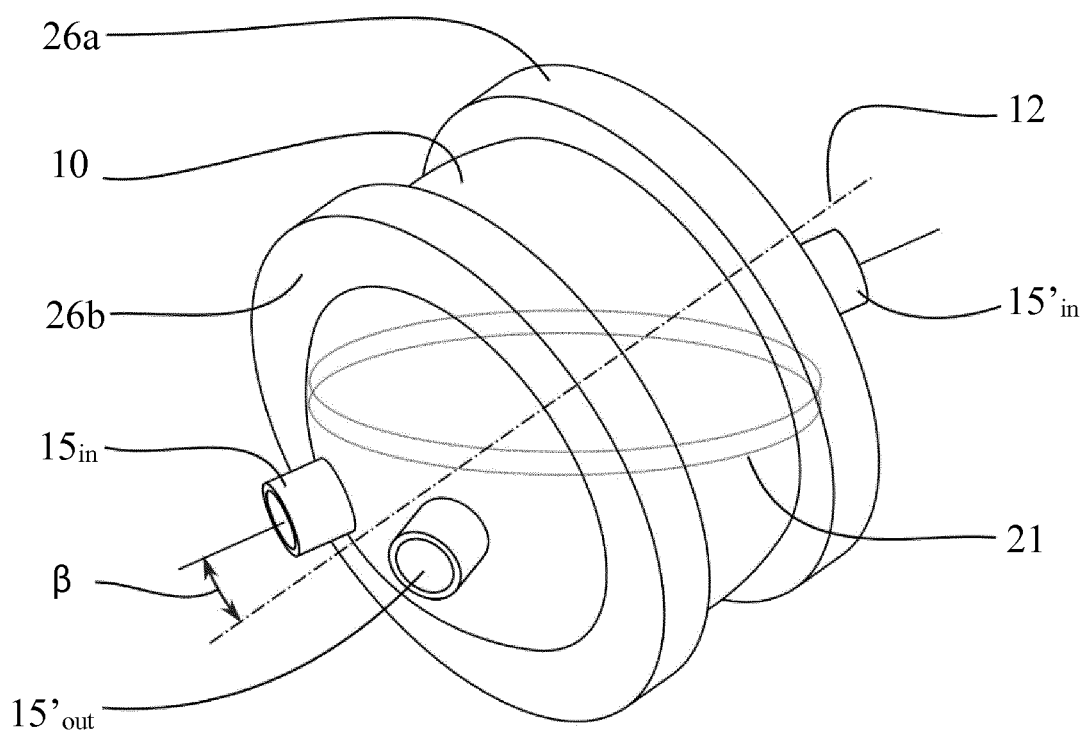
FIG. 1 shows a perspective view of the artificial heart according to a first embodiment of the invention.
Figure 2:
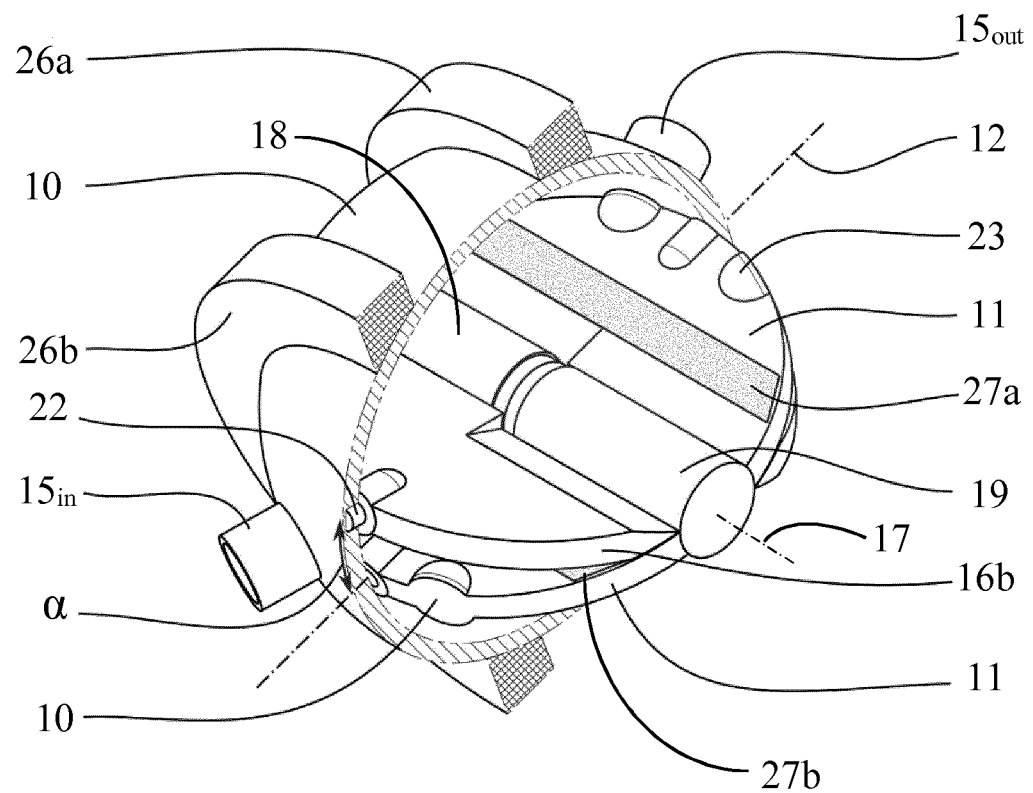
FIG. 2 shows a perspective view of the artificial heart of FIG. 1 with a partial cross-section through the pump housing.
Figure 3:
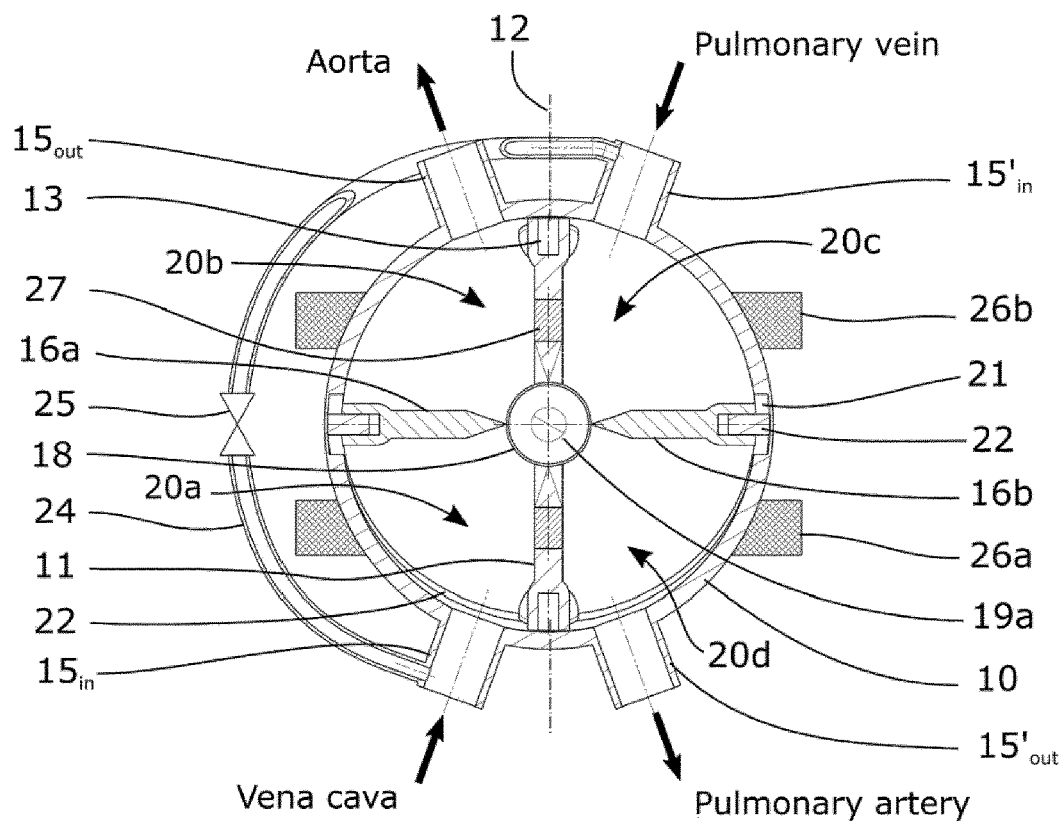
FIG. 3 shows a cross-sectional view of FIG. 1 along a plane passing through the center of the lumen of four vascular connectors, the artificial heart comprising a shunt according to a first variant.

According to a first embodiment of the invention and with reference in particular to FIGS. 1 to 3, the pump of the artificial heart comprises a housing 10 defining a spherical cavity having a radius preferably from 2.5 to 3.5 cm. A driving disc 11 is mounted inside the pump housing 10 with its circular edge tightly fitted against the inner wall of the housing. The driving disc is arranged to be rotatable about a fixed axis 12 passing through the center of the spherical cavity and which is inclined at an angle α with respect to the equator plane. This angle is typically between 10° and 30° degrees, and preferably between 10° and 20°. In this respect, two pivots 13 are securely disposed on the inner side of the wall of the pump housing, in a diametrically opposed fashion, to fit into two corresponding holes located on the edge of the driving disc 11 as shown in FIG. 3. It has to be noted that the angle α must definitely be inferior to 30° in order to guarantee the maximum useful volume (as illustrated by the grey space in FIG. 8a), which is the volume of blood ejected at each stroke. For angles from 30° and above, the stoke volume (grey space in FIG. 8b) decreases progressively. Therefore, the size of the spherical cavity must be increased progressively to guarantee an optimal flow rate of the pump. Alternatively, the number of rotations per minute of the driving disc must be increased to respect the volume constraint thereby compromising pulsatility of the flow and increasing the risk of haemolysis responsible for anaemia and nephrotoxicity due to the release of free haemoglobin.

Referring now particularly to FIG. 4a, two oscillating palettes 16a, 16b, having each a thickness of approximately 4 mm, are mounted to rotate about an axis 17 which corresponds to the diameter of driving disc 11 perpendicular to the fixed axis 12. In this respect, these palettes are connected, in a diametrically opposed fashion, to a cylinder 18 which is rotatably adjusted on a shaft 19a (FIG. 3) disposed along a diameter of the driving disc which is perpendicular to the fixed axis 12 thereby creating two parallel pumping units comprising each two variable sized chambers 20a, 20b, 20c, 20d. A circular groove 21 is arranged on the inner wall of the pump housing 10 within the equatorial plane to accommodate a protruding part 22 of each oscillating palette 16a, 16b, preferably in the form of a pin, in order to constrain these palettes to rotate about the second axis 17, through rotation of the driving disc 11 about the fixed axis 12, thereby imparting a two-degrees-of-freedom oscillating movement to each oscillating palette relative to the driving disc 11 as partly shown in FIGS. 4a to 4c. Alternatively, the protruding part 22 can be secured by means of pivots to a rotating ring housed in the groove 21, thus preventing a leak between the various chambers.

With reference to FIG. 3, the pump housing 10 is provided with four vascular connectors $15_{in}$, $15_{out}$, $15'_{in}$, $15'_{out}$, namely two inlet connectors $15_{in}$, $15'_{in}$ and two outlet connectors $15_{out}$, $15'_{out}$ having, for example, a diameter of 8 mm or more and which are configured to connect the artificial heart to the pulmonary and systemic circulation.

More specifically, one pumping unit, acting as the right heart, comprises two cavities 20a, 20d adapted to be filled with oxygen-depleted blood, these tow cavities being connected in turn to the inlet connector $15_{in}$, connectable to the vena cava, and to the outlet connector $15'_{out}$ connectable to the pulmonary artery. The other pumping unit, acting as the left heart, comprises two cavities 20b, 20c adapted to be filled with oxygen-rich blood, connected in turn to the inlet connector $15'_{in}$, connectable to the pulmonary vein, and to the outlet connector $15_{out}$, connectable to the aorta.

The center of the lumen of the four vascular connectors lie on a plane which is inclined at an angle α with respect to the equator plane and which includes the fixed axis 12 (FIG. 2). In addition, the angle β between an axis passing by the center of the lumen of each vascular connector as well as the center of the spherical cavity and the fixed axis 12 is preferably between 10° and 20°. In any case, this angle must be large enough to prevent permanent obstructions of the four vascular connectors by the driving disc 11 and small enough such that these connectors always remain clear from the pathway of the oscillating palettes 16a, 16b when the pump is operating According to this specific configuration, as partly shown in FIGS. 4a to 4c, rotation of the disc 11 through 180° imparts an angular movement to the oscillating palettes relative to the disc thereby producing two concurrent suction strokes simultaneously with two concurrent discharge strokes so as to pump blood from the corresponding inlet connector $15_{in}$, $15'_{in}$ into one of the two chambers of each pump unit while expelling blood from the other chamber of each pump unit through the corresponding outlet connector $15_{out}$, $15'_{out}$ (FIG. 3). According to this configuration, the mean flow rate of the pump is given by the following equation:

$$<Q> = \frac{\omega Vo}{2\pi^2}(\pi - 2\alpha), \text{ where } Vo = \frac{4}{3}\pi r^3$$

while the angular speed of the pump, i.e. the number of rotation of the driving disc about the fixed axis is given by:

$$\omega = \frac{2\pi^2 <Q>}{Vo(\pi - 2\alpha)}$$

and the stroke volume ΔV of each pumping unit of the pump is given by:

$$\Delta V = \frac{2}{3}R^3(\pi - 2\alpha)$$

For a mean flow rate of 5 l/min which follows the recommendation of the ASTM (American Society for Testing and Material), a radius of the spherical cavity of the pump of 3 cm and an angle α equaling to 15° for example, the driving disc must by driven about its rotation axis by the drive unit at a speed of 53 rpm where each stroke volume is theoretically 47.12 ml when the pump is operating.

Oscillating palettes 16a, 16b and the driving disc 11 must therefore be as thin as possible to reduce as much as possible the angle α, defining the dead volume, in order to improve the pulsatility of the flow delivery and to increase the pumping capacity of the pump. However, as the driving disc 11 is rotating, the vascular connectors $15_{in}$, $15_{out}$, $15'_{in}$, $15'_{out}$ must be entirely closed during an infinitesimal time at the end of each stroke to avoid blood compression and regurgitation from the arteries to the chambers of the pump or to the veins. In this respect, two bulges 23 acting as obturators, as shown particularly in FIG. 4a, are arranged on the edge of both sides of the driving disc 11, in a diametrically opposed fashion, so as to close all four vascular connectors when the rotatable disc lies within the tilted plane of these connectors. These obturators 23 advantageously allow the reduction of the angle α to 15° while acting as cardiac valves thus avoiding the use of mechanical valves as a result of which the internal structure of the pump is significantly simplified.

Figure 4:
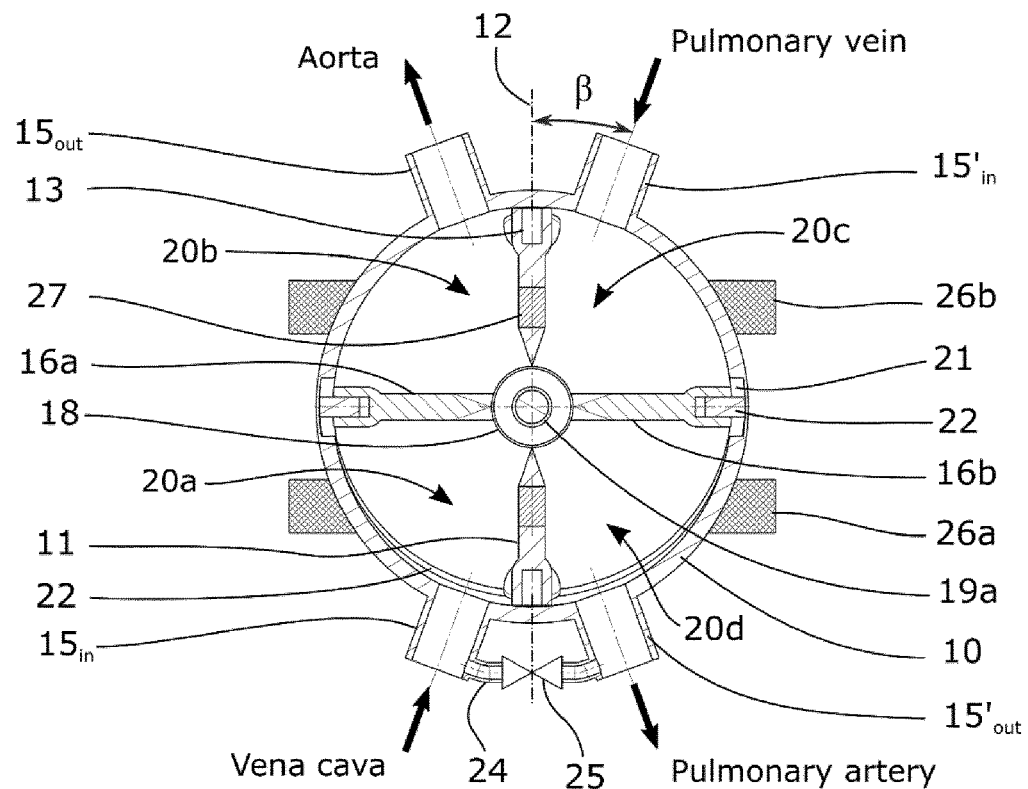
FIG. 4 shows a similar view of FIG. 3 with a shunt according to a second variant.

The stroke volume of the two pumping units of the pump, which can be assimilated to the right and left hearts, is identical because of the symmetrical pathway of the two oscillating palettes inside the pump housing. An identical stroke volume between the two pumping units is however not physiologically sustainable since, in real life, the left heart pumps 5 to 10% more volume than the right heart. The reason is that a small amount of blood passing through the aorta follows bronchial arteries and goes directly into the left atrium of the heart, through the pulmonary veins after passing through the lungs. This pattern of circulation is the exclusive systemic vascularization responsible for the nutrition of lungs cells and creates a shunt called the bronchial shunt flow. In order to avoid the excessive flow expelled by the right pumping unit through the lungs which would cause pulmonary oedema, the pump must be configured to induce a flow difference between the two pumping units in order to mimic the physiological pumping pattern of the heart. In this respect, a shunt 24 is mounted to ensure a fluid communication between two chambers. This shunt may for example be connected to allow fluid communication between the two chambers 20a, 20c of the pumping unit corresponding to the right heart as shown in FIG. 3. Alternatively, the shunt 24 may connect the two chambers 20a. 20d, as illustrated in FIG. 4. The flow through the shunt 24 can be adjusted to decrease the pumping capacity of this pumping unit, according to patient's physiological need, by mean of an adjustable valve 25. Such a shunt mechanism may also have the form of an internal shunt by adapting the sealing property between two chambers in order to provide a proper gap between the internal surface of the cavity and the oscillating palettes, for example from 100 to 500 microns, thereby permitting a controlled fluid communication between the two chambers of the pumping unit through this gap. According to the first embodiment of the invention, the driving unit of the pump, as particularly shown in FIGS. 1 and 2, comprises two multi-pole stators 26a, 26b disposed on the pump housing 10 and two permanent magnets 27a, 27b arranged on the driving disc 11 which can be regarded as the rotor. More specifically, multi-pole stators 26a, 26b lie in two parallel planes and are disposed around the pump housing 10 concentrically with respect to the first rotating axis 12 (FIG. 1). Two permanent magnets 27a, 27b are arranged on the driving disc 11 such that one permanent magnet extends across each side of the first axis 12 along a direction parallel to said axis from one edge to an opposite edge of the driving disc within the plane of the corresponding stator 26a, 26b (FIG. 2). The multi-poles stators 26a, 26b can also be embedded, at least partially, in the housing wall to reduce the distance between the stators and the permanent magnets thereby decreasing significantly the amount of energy necessary to generate the rotation of the driving disc.

Figure 6:
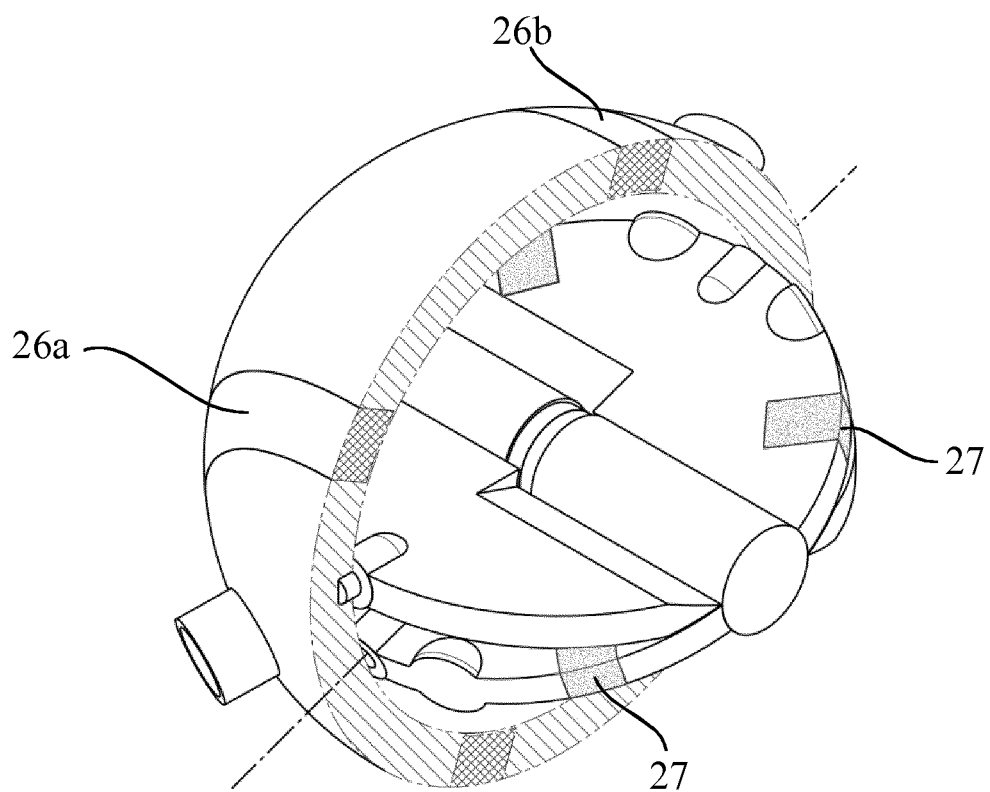
FIG. 6 shows a perspective view of the artificial heart according to a second embodiment of the invention, with a partial cross-section through the pump housing.

According the second embodiment of the invention, as shown in FIG. 6, two multi-poles stators 26a, 26b are entirely embedded the housing wall of the pump whereas four permanent magnets 27 are arranged on the driving disc 11 on both sides of its rotating axis 12 in a symmetric fashion in correspondence with the multi-pole stators 26a, 26b.

Figure 7:
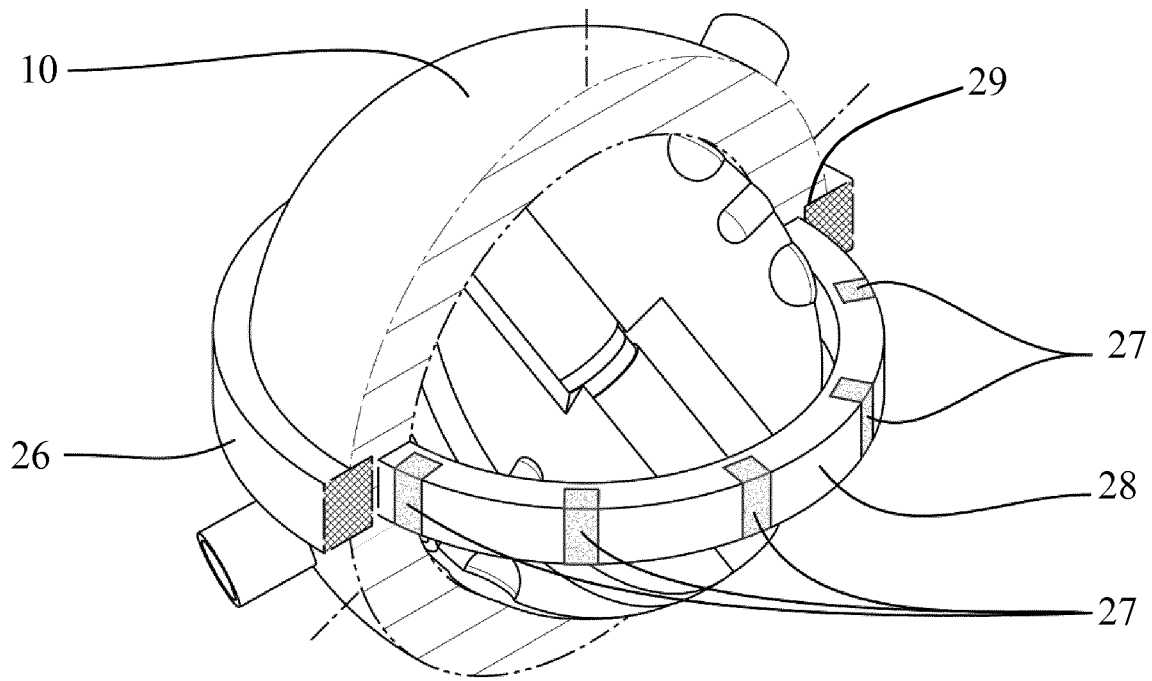
FIG. 7 shows a perspective view of the artificial heart according to a third embodiment of the invention, with a partial cross-section through the pump housing.

According to the third embodiment of the invention, as illustrated in FIG. 7, a drive ring 28 is mounted to rotate inside a circular seat 29 arranged in the equator plane of the pump housing 10 and comprises several permanent magnets 27 located around the ring 28. Both oscillating palettes 16a, 16b are hinged on the inner side of the driving ring 28 in a diametrically opposed fashion. This can be achieved for example by a pivot connected to the summit of each palette and rotatably mounted inside two apertures located on the inner side of the ring (not shown) at 180° from each other. A multi-pole stator 26 is mounted around the pump housing 10 or embedded, at least partially, in the housing wall concentrically with respect to the driving ring 28 so as to produce a rotating magnetic field inside the pump housing in order to impart a rotating movement to the driving ring 28 along its circular seat 29. Rotation of the driving ring causes the two oscillating palettes to rotate about the axis 17 while constraining their movement in the equator plane as a result of which the disc 11 is driven in rotation about the fixed axis 12.

Multi-pole stator 26, 26a, 26b according to any embodiment can be of the type used in a single, two or three-phase synchronous motor. Considering that the rotatable disc must be driven, directly (first and second embodiment) or indirectly (third embodiment), at a variable rotation speed between 40 rpm and 100 rpm to guarantee optimal flow of the pump and adequate oxygenation even at some level of activity of the patient, the drive unit further comprises a controller configured to output the appropriate signals to the coils of the stators to produce a suitable rotating magnetic field. The components of the controller may be external to the patient, or subcutaneous. For example, the controller may comprise a processor and battery power source that are completely implanted within the body such that the battery is recharged via transcutaneous energy transmission through the skin. Alternatively, a wire bundle may lead through the skin to an external controller and power supply.

In a further embodiment shown in FIG. 9, one provides the artificial heart of the present invention with a specific pulsed control which will provide the heart with a pulsatility which is similar to a physiological heart, i.e. such a control will permit to modify the driving disc rotation velocity so as to raise the blood outlet pressure upon heart-exiting moment and therefore provide a sharper profile to each heartbeat. More particularly, by providing such a pulsatility through a pulse width modulation motor, one can modify the heart beat profile to more closely correspond to a real heart.

In these figures, a) represents the angular position of the motor for a constant rotational velocity (dotted line) and an oscillating rotation velocity (solid line), while b) shows the instant heart-exiting flow rate with a constant rotational velocity motor (dotted line) and an oscillating rotation velocity motor (solid line).

EXAMPLE

Here is presented an experimental prototype as a specific example. As mentioned above, the heart is a double pump consisting of a spherical cavity split into four chambers, like the human heart chambers, by two rotating disks. The first disk has one degree of freedom and rotates around a fixed axis passing through the center of the sphere with an angle of $\theta_0$ above the equatorial plane. The second disk has two degrees of freedom as it rotates about an axis of rotation which can itself rotate about the center of the sphere within the equatorial plane. A revolute joint links both disks in a direction perpendicular to their respective primary axis of rotation. The overall system has one degree of freedom and a movement imposed to one disk entrains the other one, producing a change in the volume of the chambers.

In the present prototype, a brushed DC motor (RE 35 graphite brushes 90 watt, Maxon Motor AG, Sachseln, Switzerland) with a 14:1 planetary gearhead is coupled with a pinion which entrains a spur gear (ratio 6:1) guiding the rotation of the second disk within the equatorial plane. The continuous rotation of the motor causes the two chambers connected to the outflow tracts to increase in volume, ejecting fluid into the aorta and pulmonary artery, while the other two chambers decrease in volume, sucking fluid from the vena cava and pulmonary vein. The four openings are located in the same plane as the fixed rotation axis of the first disk, such that, every half revolution of the disk, the two filled cavities switch from being connected to the inflow tracts to the outflow tracts, and vice versa. While valves are not necessary, four static obturators with the same diameter as the openings ensure that inflow and outflow tracts are not connected to each other, even during this switch. The speed of the motor is controlled by pulse width modulation in closed loop using an optical encoder and a servo controller.

In the experimental Circulatory System, the device pumps a 37% glycerine solution reproducing the viscosity and density of blood through two parallel circuits simulating the pulmonary and systemic circulations. Each circuit consists of 8 mm diameter PVC tubing connected to the four openings of the pump, with four 1 l air pockets providing compliance. A 4 mm diameter hose connecting the left inflow and outflow reproduces the bronchial shunt, while an 8 mm diameter hose with an adjustable valve connects the right inflow and outflow to balance the bronchial shunt.

The flow rate through the systemic circulation is acquired with a magnetic inductive flowmeter (MVM-030-PA, Bronkhorst High-Tech B. V., Ruurlo, Netherlands), while piezoresistive silicon pressure sensors (ABP Series, Honeywell Inc, Morristown, N.J., USA) collect pressure in the left and right outflow tracts (resp. pAO and pAP), as well as in the left and right inflow tracts (resp. pPV and pVC). An analog to digital converter (MCP3208) is used to read the analog outputs of the motor (speed and torque), the pressure sensors voltage output, as well as the flowmeter current output converted to voltage. Each analog to digital convertor is paired with a double pole analog filter with 80 Hz cut-off frequency. A Raspberry Pi with a home-made Python software is used to collect the sensor data and control the motor. The data acquisition rate is 1 kHz. The dynamic flow rate is computed from the pressure measured at each end of the systemic circulation and the known systemic impedance.

For each frequency component $\omega$, $Q(t,\omega)=\Delta p(t,\omega)/(R+j\omega L)$ where the resistance R is the ratio of the time-averaged pressure difference and the time-averaged flow rate and the inertance L of a section of length l and area A is $L=l\rho/A$. Since the systemic circulation in the experimental circulatory system consists of a 1.05 m long 8 mm diameter hose, its inertance is 0.17 mmHg·s$^2$/ml. In-vitro test protocol. One runs the Heart by manually setting the preload at a physiological value and varying the ejection rate from 20 to 180 min$^{-1}$ with the bronchial and compensation shunts closed. For each setting, the systemic and pulmonary pressure gradients ($\Delta p_S = p_{AO} - p_{VC}$, and $\Delta p_P = p_{PA} - p_{PV}$ respectively), as well as the flow rate $Q$ in the systemic circulation are measured. The power consumption for each setting is also compared with the useful power $(\Delta p_S + \Delta p_P)Q$ and the mechanical loss measured by running the heart empty. For an ejection rate of 178 min$^{-1}$, one then opens the shunts and adjust the resistance of the compensating deviation to bring the venous pressures to physiologic values. For this setting, one measures the flow rate in the systemic circulation and the pressure at the inflow and out flow of the four chambers. Each set of measurements is phase-averaged over at least 10 cycles.

As a result, the flow rate is proportional to the rotation rate and is about 70% of the theoretical flow rate for an ideal volumetric pump. At an ejection rate of 178 min$^{-1}$, the heart pumps 5.3 l/min through the circuit with shunts closed, for a systemic maximal pressure gradient of 174 mmHg with a pulse pressure of 84 mmHg and a pulmonary maximal pressure gradient of 75 mmHg.

The device tested generates a pulsatile flow in two parallels circuits at pressures and flow values in or above the physiological range. It has been conceived for long term biventricular MCS for bridge to transplant or as total artificial heart. It has the advantages of both volumetric pumps, such as pulsatility, and centrifugal pumps, such as small dimensions and low noise. The absence of mechanical/ biological valves and the low rotation rate reduces the risk of thromboembolic events. This preliminary study endorses the feasibility of a single valveless device acting as total artificial heart.

The invention claimed is:

1. Artificial heart comprising a pump, said pump comprising:
    a housing (10) defining a substantially spherical cavity and comprising four vascular connectors (15$_{in}$, 15$_{out}$, 15'$_{in}$, 15'$_{out}$), namely two inlet connectors (15$_{in}$, 15'$_{in}$) and two outlet connectors (15$_{out}$, 15'$_{out}$) to connect the pump to the pulmonary and systemic circulation;
    a rotatable disc (11) housed within the housing (10) and secured to rotate about a fixed axis (12);
    two oscillating palettes (16a, 16b) mounted to rotate about an axis (17) intersecting the fixed axis (12) at the center of the spherical cavity, said axis (17) being rotatable within a plane perpendicular to the fixed axis (12), wherein said palettes (16a, 16b) are connected together and are arranged on both sides of the rotatable disc (11), in a diametrically opposed fashion, to create two pumping units comprising each two variable sized chambers (20a, 20b, 20c, 20d) in fluid communication with one corresponding inlet and outlet connector respectively,
    constrain means (21) configured to cause an oscillating movement of each oscillating palette (16a, 16b) relative to the rotatable disc (11), when the pump is operating, in order to produce simultaneously two suction strokes and two discharge strokes, so as to pump blood from the inlet connectors (15$_{in}$, 15'$_{in}$) into one chamber (20a, 20c) of each pumping unit while expelling blood from the other chamber (20b, 20d) of each pumping unit through the outlet connectors (15$_{out}$, 15'$_{out}$), and
    a drive unit configured to operate the pump,
    characterized in that
said drive unit is configured to produce a rotating magnetic field inside the pump housing (10).

2. The artificial heart according to claim 1, characterized in that the drive unit comprises at least one multi-pole stator (26; 26a, 26b) mounted around the pump housing (10) or embedded, at least partially, in the housing wall to generate the rotating magnetic field.

3. The artificial heart according to claim 2, characterized in that the drive unit further comprises at least one permanent magnet (27, 27a, 27b) arranged on the rotatable disc (11) on both sides of the fixed axis (12) in correspondence with two multi-pole stators (26a, 26b) mounted around the pump housing (10) or embedded, at least partially, in the housing wall so as to impart a rotating movement to the rotatable disc (11) through said rotating magnetic field.

4. The artificial heart according to claim 3, characterized in that the at least one permanent magnet (27a, 27b) is arranged to extend along an axis parallel to the fixed axis (12) of the rotatable disc (11) from one edge to an opposite edge of said disc (11).

5. The artificial heart according to claim 3, characterized in that two permanent magnets (27) are arranged on the rotatable disc (11) on both sides of the fixed axis (12) in a symmetric fashion.

6. The artificial heart according to claim 2, characterized in that a rotatable ring (28) is mounted inside a circular seat (29) arranged within an equator plane which divides the pump housing (10) in two hemispheres, wherein said rotatable ring (28) is connected to both oscillating palettes (16a, 16b) and comprises several permanent magnets (26) and in that a multi-pole stator (26) is mounted around the pump housing (10) or embedded, at least partially, in the housing wall concentrically with respect to the rotatable ring (28).

7. The artificial heart according to claim 1, characterized in that the fixed axis (11) is inclined at an angle α with respect to an equator plane which divides the pump housing (10) in two hemispheres, wherein the angle α is typically between 10° and 30° degrees, preferably between 10° and 20°.

8. The artificial heart according to claim 1, characterized in that a shunt (24) is arranged to ensure fluid communication between two chambers (20a, 20b) for balancing the pulmonary and systemic circulations, wherein the shunt (24) comprises a valve (25) for adjusting the flux through said shunt (24).

9. The artificial heart according to claim 1, characterized in that four obturators (23) are arranged on the edge of both sides of the rotatable disc (11), in a diametrically opposed fashion, so as to close all four vascular connectors (15$_{in}$, 15$_{out}$, 15'$_{in}$, 15'$_{out}$) when the rotatable disc (11) lies within the tilted plane of these connectors (15$_{in}$, 15$_{out}$, 15'$_{in}$, 15'$_{out}$), wherein the size of the obturators (23) is adapted to seal entirely the vascular connecters (15$_{in}$, 15$_{out}$, 15'$_{in}$, 15'$_{out}$).

10. Artificial heart comprising a pump, said pump comprising:
    a housing (10) defining a substantially spherical cavity and comprising four vascular connectors (15$_{in}$, 15$_{out}$, 15'$_{in}$, 15'$_{out}$), namely two inlet connectors (15$_{in}$, 15'$_{in}$) and two outlet connectors (15$_{out}$, 15'$_{out}$) to connect the pump to the pulmonary and systemic circulation;
    a rotatable disc (11) housed within the housing (10) and secured to rotate about a fixed axis (12);
    two oscillating palettes (16a, 16b) mounted to rotate about an axis (17) intersecting the fixed axis (12) at the center of the spherical cavity, said axis (17) being rotatable within a plane perpendicular to the fixed axis (12), wherein said palettes (16a, 16b) are connected together and are arranged on both sides of the rotatable disc (11), in a diametrically opposed fashion, to create two pumping units comprising each two variable sized chambers (20a, 20b, 20c, 20d) in fluid communication with one corresponding inlet and outlet connector respectively, constrain means (21) configured to cause an oscillating movement of each oscillating palette (16a, 16b) relative to the rotatable disc (11), when the pump is operating, in order to produce simultaneously two suction strokes and two discharge strokes, so as to pump blood from the inlet connectors ($15_{in}$, $15'_{in}$) into one chamber (20a, 20c) of each pumping unit while expelling blood from the other chamber (20b, 20d) of each pumping unit through the outlet connectors ($15_{out}$, $15'_{out}$), and a drive unit configured to operate the pump, characterized in that the pump further comprises a shunt (24) which is arranged to ensure fluid communication between two chambers of the pump for balancing the pulmonary and systemic circulation, wherein the shunt (24) preferably comprises a valve (25) for adjusting the flux though said shunt (24).

\* \* \* \* \*